US009173545B2

(12) United States Patent
Schoonbaert

(10) Patent No.: US 9,173,545 B2
(45) Date of Patent: Nov. 3, 2015

(54) LARYNGOSCOPIC DEVICE

(76) Inventor: Ian Schoonbaert, Pembrooke (CA)

(*) Notice: Subject to any disclaimer, the term of this patent is extended or adjusted under 35 U.S.C. 154(b) by 505 days.

(21) Appl. No.: 13/541,834

(22) Filed: Jul. 5, 2012

(65) Prior Publication Data
US 2013/0018227 A1 Jan. 17, 2013

Related U.S. Application Data

(60) Provisional application No. 61/506,412, filed on Jul. 11, 2011.

(51) Int. Cl.
A61B 1/267 (2006.01)
A61B 1/00 (2006.01)
A61B 1/06 (2006.01)

(52) U.S. Cl.
CPC .......... A61B 1/00052 (2013.01); A61B 1/0669 (2013.01); A61B 1/267 (2013.01)

(58) Field of Classification Search
CPC .... A61B 1/00052; A61B 1/267; A61B 1/053; A61B 1/0676
USPC ................................. 600/185–200
See application file for complete search history.

(56) References Cited

U.S. PATENT DOCUMENTS 5,363,838 A * 11/1994 George .......................... 600/120
5,665,052 A * 9/1997 Bullard .......................... 600/194
7,946,981 B1 * 5/2011 Cubb ............................. 600/194
8,388,524 B2 * 3/2013 Bullard .......................... 600/188
8,414,481 B2 * 4/2013 Hakanen et al. .............. 600/196
8,715,172 B1 * 5/2014 Girgis ............................ 600/188
8,721,535 B2 * 5/2014 Chen ............................. 600/188
2002/0022769 A1 * 2/2002 Smith et al. ................... 600/188
2003/0088156 A1 * 5/2003 Berci et al. ................... 600/188
2003/0195390 A1 * 10/2003 Graumann .................... 600/188
2009/0270684 A1 * 10/2009 Nielsen et al. ................ 600/193
2010/0094090 A1 * 4/2010 Mejia ............................ 600/120
2011/0270038 A1 * 11/2011 Jiang et al. ................... 600/188
2013/0060090 A1 * 3/2013 McGrath et al. ............. 600/188

FOREIGN PATENT DOCUMENTS

EP 2380486 A1 * 10/2011 ............. A61B 1/267

* cited by examiner

Primary Examiner — Anu Ramana
(74) Attorney, Agent, or Firm — Ryan W. Dupuis; Kyle R. Satterthwaite; Ade & Company Inc.

(57) ABSTRACT

A laryngoscopic device includes a laryngoscope video blade and a handle module arranged to support the video blade or auxiliary direct laryngoscopy blades interchangeably thereon. The video blade includes a camera and contacts for receiving electrical power from the handle module while outputting video to the handle module from the camera. The handle module can also provide electrical power to a light source on the video blade or include its own light source to be conveyed to a light guide of a blade coupled to the handle module. The laryngoscopic device also includes a display monitor which can be removably coupled to an output of the handle module to display video generated by the video blade camera. The handle module can be used alone with non-video blades or readily converted to a video laryngoscopic device by replacing the non-video blade with a video blade and connecting the display monitor.

15 Claims, 8 Drawing Sheets

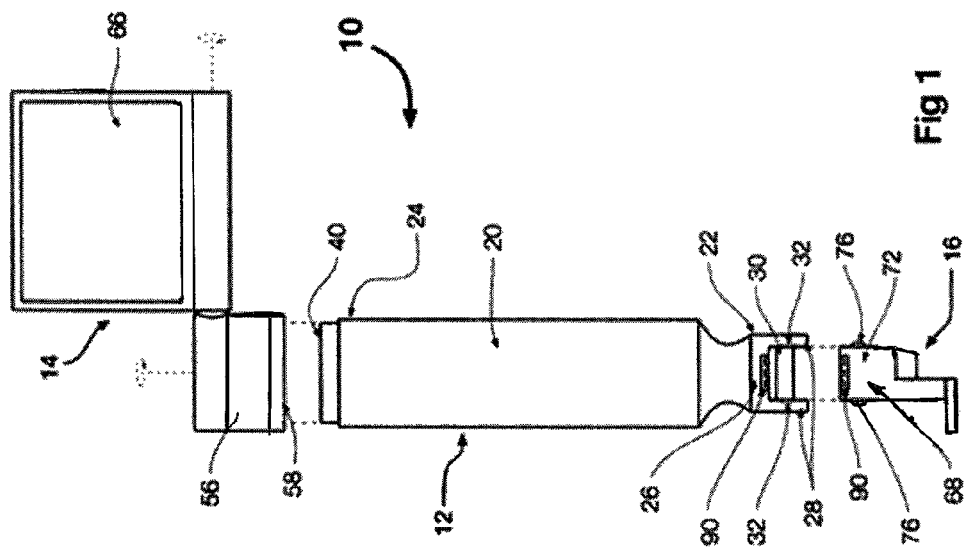

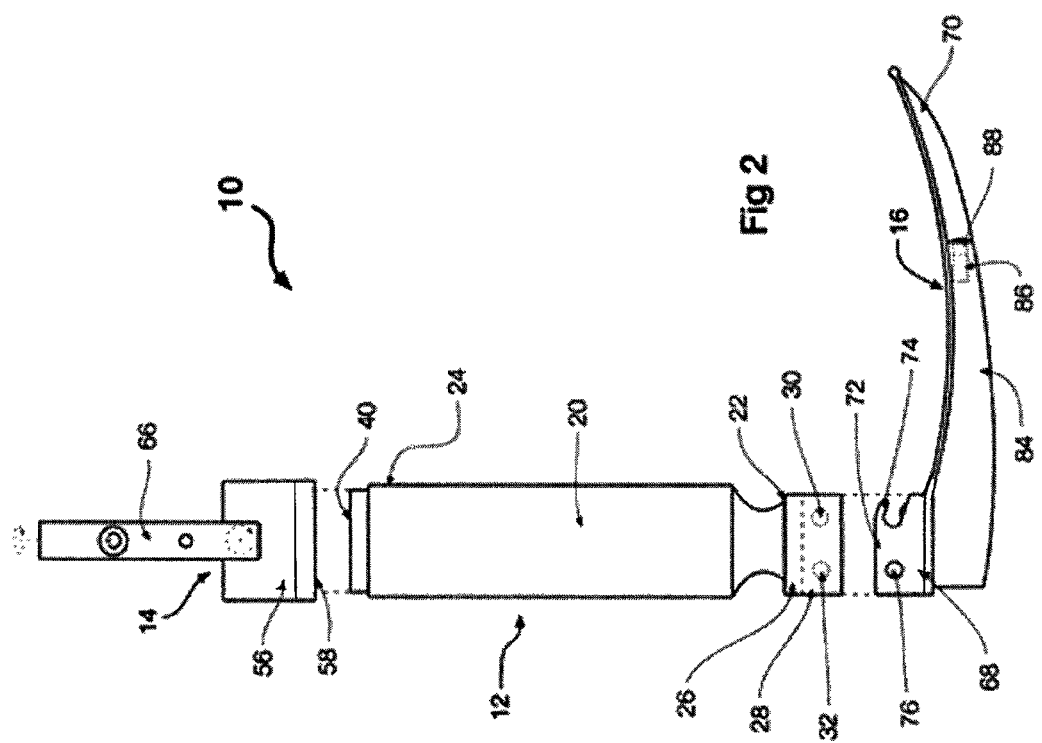

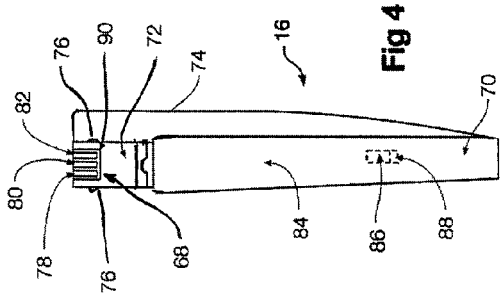
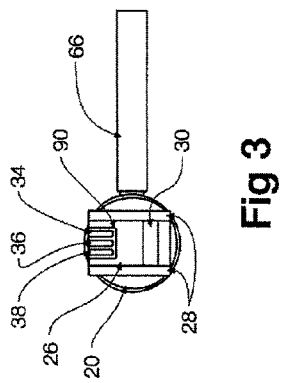
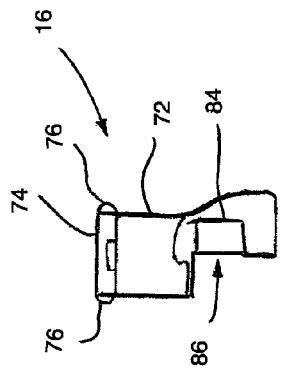

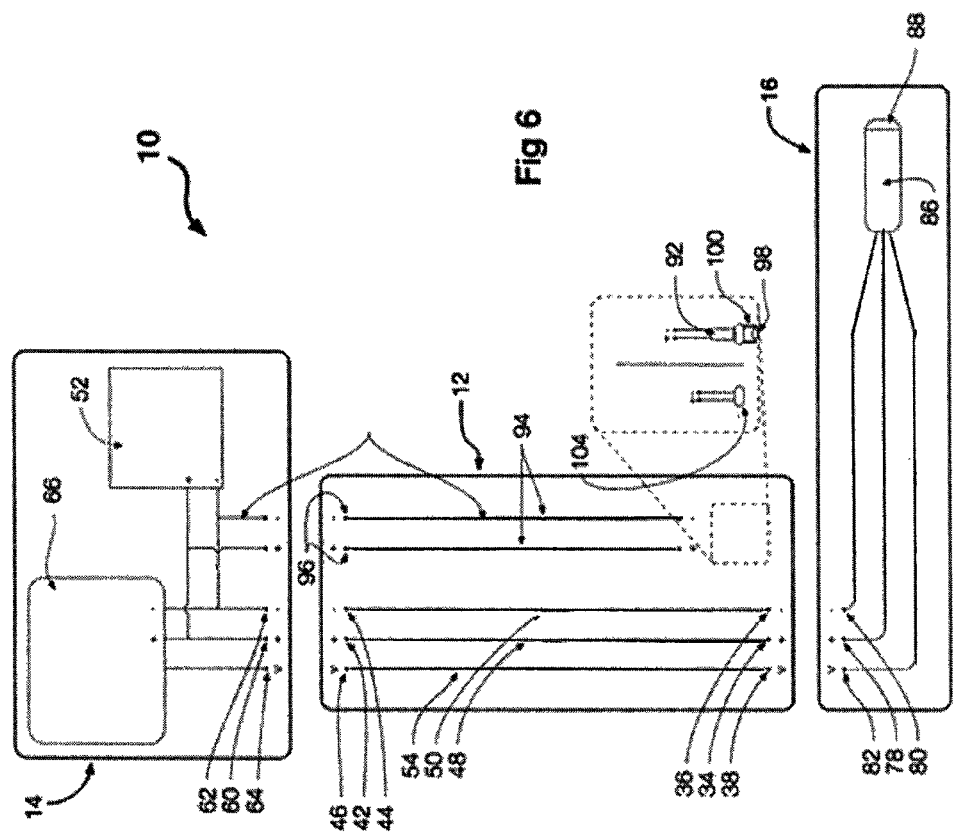

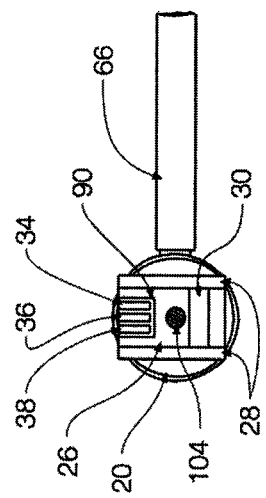
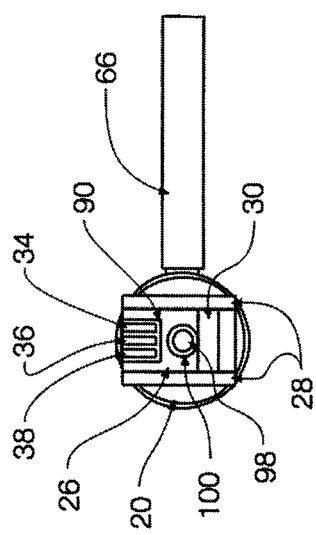

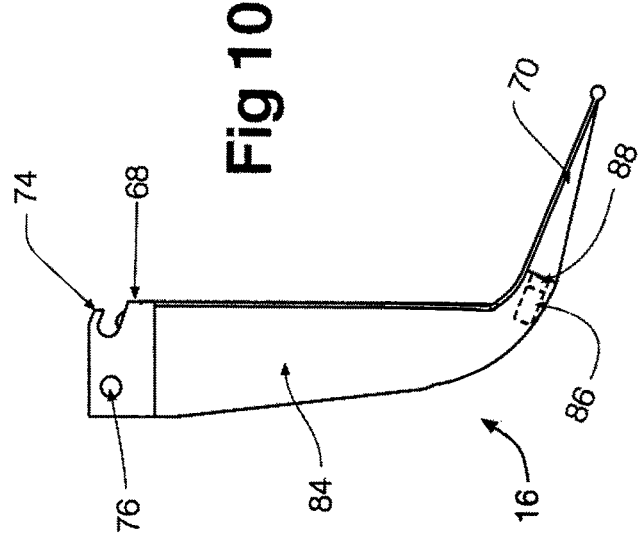
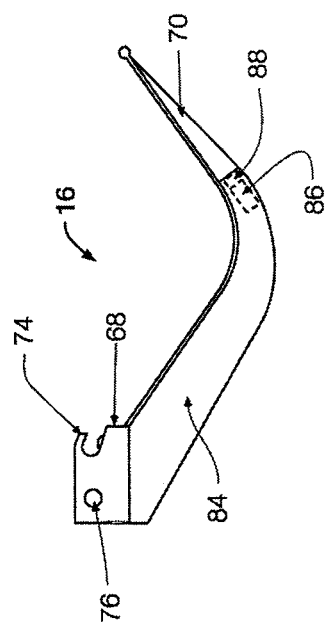

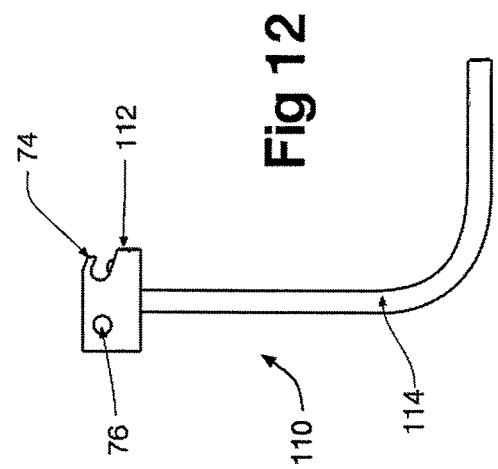
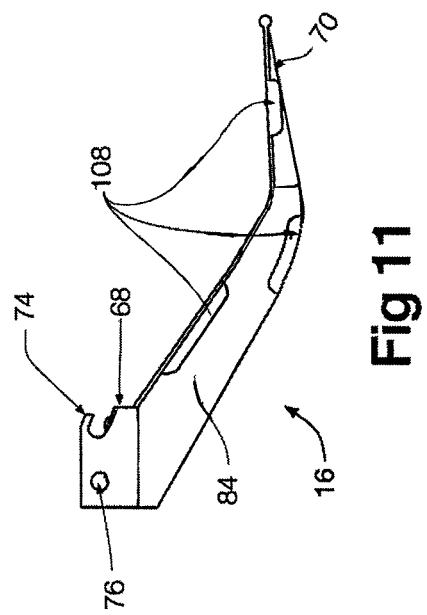
Fig 12
Fig 11

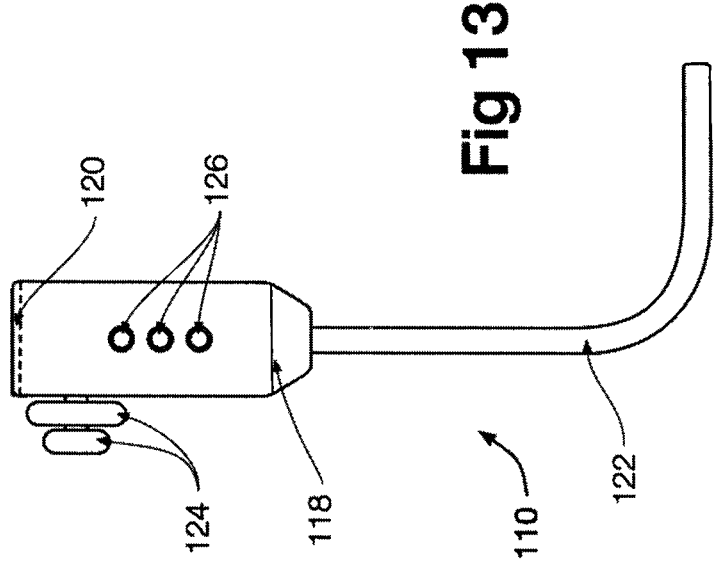

LARYNGOSCOPIC DEVICE

This application claims the benefit under 35 U.S.C.119(e) of U.S. provisional application Ser. No. 61/506,412, filed Jul. 11, 2011.

FIELD OF THE INVENTION

The present invention relates to a laryngoscopic device comprising a handle and a laryngoscope blade for insertion into an airway of a person, and more particularly the present invention relates to a laryngoscopic device comprising a handle supporting video functionality which interchangeably supports video and non-video enabled blades thereon.

BACKGROUND

Video laryngoscopy is a relatively new development in the field of anaesthesia. Traditional DIRECT LARYNGOSCOPY (DL) involves using a blade with a light at the end to obtain a view of the glottis via a direct view from the maxillary teeth to the vocal cords. This allows passage of an endotracheal (ET) tube under direct vision. Direct laryngoscopy involves alignment of the oral, pharyngeal and tracheal axes to produce this view. RIGID INDIRECT LARYNGOSCOPY (RIL) involves obtaining a view of the glottis without alignment of the oral, pharyngeal and tracheal axes. This view has been obtained with prisms, mirrors and fiber-optics in the past and more recently with video cameras (i.e. CMOS or CCD cameras). Although initially used primarily as rescue devices (i.e. when direct laryngoscopy has failed) video laryngoscopes are being increasingly used as primary devices as well. Unfortunately one barrier to the use of video laryngoscopes is that they are expensive to buy and so are in limited supply in many health care facilities and even more limited supply in the pre-hospital setting. This is despite the fact that they have been shown to be highly effective in the hands of anaesthetists, non-anaesthetists, experienced and non-experienced providers alike in numerous studies of both human's and manikins. Outside of expense as a barrier to these devices being stocked another barrier to their use is that these devices have only one possible use rather than being multifunctional. This means that in usual practice direct laryngoscopy is the primary technique with VIDEO-LARYNGOSCOPY (VL) as a secondary technique and supra-glottic devices, fiber-optic bronchoscopes or surgical airways following after this if unsuccessful. No device has been able to bridge the barriers between techniques and become truly multifunctional. Multi functionality would allow providers to quickly and seamlessly bridge between techniques with the same device. It would also allow providers to customize their device to their particular skills.

SUMMARY OF THE INVENTION

According to a one aspect of the invention there is provided a laryngoscopic device comprising:
 a laryngoscope video blade comprising:
  an elongate body portion spanning between a coupling portion at a first end and a tip portion at an opposing second end so as to be arranged for insertion into an airway opening of a patient, the coupling portion including a positive contact, a negative contact, and a video output contact; and
  a camera supported on the body portion adjacent the tip portion so as to be arranged to generate a video signal, the camera being operatively connected to the positive contact, the negative contact, and the video output contact of the coupling portion of the laryngoscope video blade;
 an electrical power source including positive and negative terminals;
 a handle module which is elongate between a working end and an opposing output end so as to be arranged for gripping in a hand of a user;
 the working end of the handle module being arranged for mating connection with the coupling portion of the laryngoscope video blade in a coupled position;
 the working end of the handle module including a positive contact, a negative contact and a video output contact supported thereon, the contacts on the handle module being arranged for mating connection to respective ones of the positive contact, the negative contact and the video output contact of the laryngoscope blade in the coupled position thereof and the contacts on the handle module being arranged to allow the laryngoscope video blade including the camera to be readily separable from the handle module together with the contacts on the body portion of the laryngoscope video blade;
 the output end of the handle module being arranged to output the video signal for viewing by a user;
 the handle module further comprising a positive electrical conduit arranged for communicating the positive contact of the working end of the handle module to the positive terminal of the power source, a negative electrical conduit arranged for communication between the negative contact of the working end of the handle module and the negative terminal of the power source, and a video output conduit arranged for communication between the video output contact at the working end of the handle and the output end of the handle module.

The device may also be used with a laryngoscope auxiliary blade having an elongate body portion spanning between a coupling portion at a first end and a tip portion at an opposing second end and being shaped so as to be arranged for direct laryngoscopy in which the auxiliary blade is interchangeable with the video blade.

When the handle module includes a light source, the auxiliary blade may include an optical light guide arranged for mating alignment with the light source of the handle module in a coupled position of the auxiliary blade on the handle module in which the optical light guide is arranged to convey light from the light source in the handle to the tip portion.

When the handle module includes auxiliary contacts at the working end, the auxiliary blade may also include a light source at the tip portion which is connected to auxiliary contacts at the coupling portion of the auxiliary blade in which the auxiliary contacts of the auxiliary blade and the auxiliary contacts of the working end of the handle module are arranged for mating alignment in a coupled position of the auxiliary blade on the handle module so as to be arranged to convey an electrical signal from the handle module to the light source of the auxiliary blade in the coupled position.

The working end of the handle module may include a coupling pin and a pair of sockets spaced from the coupling pin. In this instance the coupling portion of the video blade preferably includes a hook arranged for hooking onto the coupling pin and a pair spring pins arranged for selective mating connection with the pair of sockets in the coupled position of the video blade on the handle module such that the video blade is interchangeable with a conventional laryngoscope blade having a hook and a pair of spring pins.

The laryngoscopic device preferably further comprises a monitor module which includes a housing having a coupling portion arranged to be selectively coupled to the output end of the handle module such that the monitor module is readily separable from the handle module. The monitor module preferably comprises a video display monitor arranged to display the video signal which is generated by the camera and communicated through the video output conduit of the handle module.

When the monitor module supports the power source thereon, preferably the coupling portion of the monitor module and the output end of the handle module each comprise a positive contact, a negative contact, and a video output contact which are arranged for mating connection with one another in a coupled position of the monitor module on the handle module. In this instance the positive contact, the negative contact and the video output contact at the output end of the handle module are coupled to the positive electrical conduit, the negative electrical conduit and the video output conduit respectively. Similarly, the positive contact, the negative contact and the video output contact of the monitor module are coupled to the positive terminal of the power source, the negative terminal of the power source and the video display monitor respectively.

The laryngoscopic may also be used in combination with a bronchoscope device comprising a coupling portion arranged to be coupled to the monitor module so as to be interchangeable with the handle module. In this instance the bronchoscope device preferably includes a camera arranged to generate a video signal, a video output contact connected to the camera which is arranged for mating connection with the video output contact of the monitor module in a coupled position of the monitor module on the bronchoscope device, and auxiliary electrical contacts arranged for mating connection with the positive and negative contacts of the monitor module so as to be arranged to supply electrical power to the camera of the bronchoscope device.

In some embodiments the main body portion includes a main portion between the coupling portion and the tip portion which is inclined relative to a longitudinal axis of the handle module and the tip portion is inclined relative to the main portion.

Alternatively the main body portion may include a main portion between the coupling portion and the tip portion which is generally coaxial with a longitudinal axis of the handle module with the tip portion being inclined relative to the main portion.

In some instances the main body portion includes a plurality of tube guides at spaced apart positions between the coupling portion and the tip portion so as to be arranged to support a tube member alongside the body portion.

The laryngoscopic device may also be used in combination with a stylet device comprising a coupling portion configured similarly to the coupling portion of the video blade such that the video blade and the stylet device are arranged to be interchangeably mounted on the handle module. The stylet device preferably comprises a probe member supporting a camera at a tip portion thereof opposite the coupling portion in which the camera is connected to a video output contact at the coupling portion of the stylet device. The video output contact of the stylet device is preferably arranged for mating alignment with a video output contact on the working end of the handle module in a coupled position of the stylet on the handle module so as to be arranged for communicating a video signal generated by the camera of the stylet to the video output conduit of the handle module.

According to furthers aspects of the present invention there is provided a laryngoscopic device comprising:

a laryngoscope video blade comprising:
  an elongate body portion spanning between a coupling portion at a first end and a tip portion at an opposing second end so as to be arranged for insertion into an airway opening of a patient;
  the coupling portion of the laryngoscope video blade being arranged for mating connection with the working end of the handle module in a coupled position;
  the coupling portion including a positive contact, a negative contact, and a video output contact supported thereon, the contacts on the coupling portion of the laryngoscope video blade being arranged for mating connection to respective ones of the positive contact, the negative contact and the video output contact of the handle module in the coupled position thereof and the contacts on the coupling portion of the laryngoscope video blade being arranged to allow the laryngoscope video blade to be readily separable from the handle module together with the contacts on the working end of the handle module;
a camera, with an intrinsic light source and anti-fogging capability, supported on the body portion adjacent the tip portion so as to be arranged to generate a video signal, the camera being operatively connected to the positive contact, the negative contact, and the video output contact of the coupling portion of the laryngoscope video blade;
a handle module comprising:
an elongated portion between a working end and an opposing output end so as to be arranged for gripping in a hand of a user;
the working end of the handle module being arranged for mating connection with the coupling portion of the laryngoscope video blade in a coupled position;
the working end of the handle module including a positive contact, a negative contact and a video output contact supported thereon, the contacts on the handle module being arranged for mating connection to respective ones of the positive contact, the negative contact and the video output contact of the laryngoscope blade in the coupled position thereof and the contacts on the handle module being arranged to allow the laryngoscope blade to be readily separable from the handle module together with the contacts on the body portion of the laryngoscope video blade;
the handle module further comprising a positive electrical conduit arranged for communication between the positive contact of the working end of the handle module and the positive contact of the output end of the handle module, a negative electrical conduit arranged for communication between the negative contact of the working end of the handle module and the negative contact of the output end of the handle module, and a video output conduit arranged for communication between the video output contact at the working end of the handle and the video output contact at the output end of the handle module;
the output end of the handle module being arranged for mating connection with the coupling portion of the monitor module in a coupled position;
the output end of the handle module being arranged to output the video signal for viewing by a user via the monitor module;
the positive contact, the negative contact and the video output contact at the output end of the handle module are coupled to the positive electrical conduit, the negative electrical conduit and the video output conduit respectively;
the output end of the handle module including a positive contact, a negative contact and a video output contact supported thereon, the contacts on the handle module being arranged for mating connection to respective ones of the positive contact, the negative contact and the video output contact of the monitor module in the coupled position thereof and the contacts on the handle module being arranged to allow the monitor module to be readily separable from the handle module together with the contacts on the housing of the monitor module;

the output end of the handle module in some forms of the device including a positive auxiliary contact and a negative auxiliary supported thereon, the contacts on the handle module being arranged for mating connection to respective ones of the positive auxiliary contact and negative auxiliary contact of the monitor module in the coupled position thereof and the contacts on the handle module being arranged to allow the monitor module to be readily separable from the handle module together with the contacts on the housing of the monitor module;

the handle module in some forms of the device further comprising an auxiliary electrical conduit arranged for communication between the positive auxiliary contact and negative auxiliary contact of the output end of the handle module and the auxiliary interface of the working end of the handle module;

the handle module in some forms of the device further comprising an auxiliary interface of the working end of the handle module, which when coupled to an auxiliary laryngoscope blade provides either a power source to said auxiliary laryngoscope blade or provides an LED light source to said auxiliary laryngoscope blade depending on the type of handle module and type of auxiliary laryngoscope blade;

a monitor module comprising:

a housing having a coupling portion arranged to be selectively coupled to the output end of the handle module;

a video display monitor arranged to display the video signal generated by the camera in the laryngoscope video blade and communicated through the video output conduit of the handle module to the monitor module;

a power source therein arranged to provide power to the video display in the monitor module itself, the camera and LED light source in the laryngoscope video blade through the positive and negative electrical conduits of the handle module and to any light source in the handle module or auxiliary laryngoscope blade through the auxiliary electrical conduit;

the positive contact, the negative contact and the video output contact of the monitor module being coupled to the positive terminal of the power source, the negative terminal of the power source and the video display monitor respectively;

a coupling portion of the monitor module consisting of a positive contact, a negative contact, a video output contact, a positive auxiliary contact and a negative auxiliary contact, which are arranged for mating connection with the same contacts on the output end of the handle module in a coupled position of the monitor module on the handle module.

The novel video laryngoscope outlined here provides maximal flexibility and versatility to the user and the health care facility purchasing the device. From the users point of view there is a seamless transition between traditional direct laryngoscopy to indirect video laryngoscope for patients of all ages, shapes and sizes. As an example, an emergency department physician might be using this NOVEL VIDEO-LARYNGOSCOPE (NVL) with a video/fiberoptic handle module coupled to a standard non-video Macintosh fiber-optic blade. In this configuration the device is essentially a standard direct laryngoscope. If an unanticipated difficult airway arises currently a video-laryngoscope might be called upon as a rescue device. With the NVL, the standard blade is removed and an attempt with a Macintosh video blade or a indirect video blade can be made immediately without needing to change devices, just blades. Current practice with currently available VLs requires calling for the VL device (which might not be in the department), hoping that the VL is available (as it may already be in use) and hoping that the correct sized blade is available. With the NVL, these issues are void. By making the device modular, blades of all shapes, types and sizes are at the finger tips of the user. Despite the aforementioned emergency department example (starting with a non-video blade), the ideal use of the NVL in this author's opinion would be starting with the monitor/handle module and a Macintosh video blade. The operator would first attempt standard direct laryngoscopy and intubation without using the monitor, if unsuccessful use the monitor with the same blade and if still unsuccessful trade the Macintosh video blade for an indirect video blade. This would all happen in an easy, logical fashion. With time, the individual user can also customize the device with video blades with a tube channel if desired, obtain other attachments including flexible stylet for confirmation of tube positions, intubating video stylet or even a flexible fiber-optic laryngoscope. The intended user is anyone performing intubation from the anaesthetist in the operating room suite to the medic on the battlefield.

From the perspective of the health care facility who may be investing in this device the benefits are numerous. First of all it will provide that facility with up to date equipment for use in their operating rooms, emergency rooms, intensive care units and in the pre-hospital setting. The importance of this cannot be understated as the current availability of VLs in practice is abhorrent given their ease of use and high success rates in the hands of providers of all skill levels. Although there would be an initial expense in procuring the NVL, this could easily be spread out over years due to the nature of the NVL. There are many procurement options for facilities. Initially, facilities could purchase the NVL monitor/handle module combo of their choosing with a limited number of video blades for each and every airway cart. These NVL monitor/handle module combos would be used with existing non-video blades the majority of the time with video blades being used in the back up role. Slowly, with time facilities could purchase more blades and attachments as they saw fit, perhaps eventually completely replacing their non-video blades. Alternatively facilities could purchase one 'NVL airway kit' for each area of the hospital (OR, ER, ICU, etc.). That NVL kit could consist of a NVL monitor/handle module combo, a larger number of blades and a variety of attachments. This could be used as needed for difficult airways. As more money became available more of these kits could be procured to the point that all users had an NVL available for all intubations. By eventually transitioning to NVL for every provider, in both the pre-hospital and hospital setting, many failed airways will be avoided.

Various embodiments of the invention will now be described in conjunction with the accompanying drawings in which:

BRIEF DESCRIPTION OF THE DRAWINGS

FIG. 1 is a rear elevational view of a first embodiment of the laryngoscopic device.

FIG. 2 is a side elevational view of the device of FIG. 1.

FIG. 3 is an end elevational view of the handle module of the device of FIGS. 1 and 2.

FIG. 4 is an end elevational view of the video blade for connection to the handle module of FIG. 3.

FIG. 5 is an end elevational view of the video blade of FIG. 4.

FIG. 6 is a schematic representation of the electrical components of the device of FIG. 1.

FIG. 7 is an end elevational view of an alternative embodiment of the handle module.

FIG. 8 is an end elevational view of a further embodiment of the handle module.

FIGS. 9 through 11 are side elevational views of different auxiliary blades which are interchangeable with one another and the video blade of FIG. 4.

FIG. 12 is a side elevational view of an auxiliary tool arranged to be interchangeably mounted with the video blade on the handle module.

FIG. 13 is a side elevational view of a bronchoscope device arranged to be interchangeable with the handle module attached directly on the monitor module.

In the drawings like characters of reference indicate corresponding parts in the different figures.

DETAILED DESCRIPTION

Referring to the accompanying figures, there is illustrated a laryngoscopic device generally indicated by reference numeral 10. The device 10 typically comprises a modular kit including one or more variations of handle modules 12, a monitor module 14, blades 16 and other auxiliary tools arranged to be interchangeably connected with one another. The common features of the various embodiments will first be described herein.

In each instance, the handle module generally comprises a body 20 which is elongated and generally cylindrical in shape about a longitudinal axis extending between a working end 22 and an opposite output end 24 so as to be suitably arranged for gripping in a single hand of a user. The working end 22 includes a coupling portion formed thereon which comprises a base plate 26 at the end of the body and two side plates 28 extending outward in the longitudinal direction from the base plate at parallel and spaced apart positions. A coupling pin 30 spans perpendicularly between the two side plates spaced outwardly from the base plate onto which one of the blades 16 may be hooked in a coupled position. The side plates 28 further comprise respective bores 32 formed therein on the inner surfaces for mating connection with spring pins of the blade coupled thereto. In this manner, the coupling portion of the handle is arranged for mating connection with a variety of conventional laryngoscope blades having a hook and spring pins.

The base plate of the coupling portion of the handle module further includes a positive contact 34, a negative contact 36 and a video output contact 38 mounted thereon. These contacts are arranged for mating with respective contacts of a blade coupled to the coupling portion of a handle module in a working position.

The output end of the handle module also includes a coupling portion 40 arranged for mating connection with the monitor module 14 by a readily releasable mechanical attachment which may include a threaded connection, a pin connection, a friction fit connection, or any other suitable mechanical fastening for example. The output end of the handle portion similarly includes a positive contact 42, a negative contact 44 and a video output contact 46. The handle module further includes a positive electrical conduit 48 coupled between the positive contact at opposing ends of the handle module and a negative electrical conduit 50 coupled between the negative contacts at opposing ends of the handle module. The conduits serve to connect the positive and negative contacts at the working end of the handle module to respective positive and negative terminals of a power source 52 supported in the monitor module.

The handle module further includes a video conduit 54 extending between the video output contacts at opposing ends of the handle body. The video conduit 54 communicates a video output signal from a blade attached to the working end of the handle module to the monitor module connected at the opposing end of the handle module.

The monitor module 14 includes a housing 56 having a suitable connector 58 which is arranged to mechanically couple the housing to the output end of the handle body. The housing 56 includes a positive contact 60, a negative contact 62 and a video output contact 64 arranged to align with respective contacts at the output end of the handle module when the connector 58 of the monitor module connects the housing 56 to the handle body in a coupled position. The contacts remain readily releasable with one another when the monitor module is released from the handle module. The positive and negative contacts are connected internally within the housing 56 to the positive and negative contacts of the power source in the form of a rechargeable battery mounted within the housing. The monitor module also includes a connector for connection to a suitable charging module for recharging the battery, as well as control buttons for controller powering on and off of the device and the like.

The monitor module further includes a video monitor 66 arranged to display a video image thereon representing a video signal which is output from the blade through the video output conduit of the handle and into the video output contact of the monitor module. The video monitor 66 is pivotally supported on the housing such that the monitor swivels about a first pivot axis which is perpendicular to a longitudinal axis of the handle and is substantially parallel to a lateral axis of the coupling pin at the working end of the handle module. The monitor 66 is also pivotal about a second pivot axis which is substantially co-axial with the longitudinal axis of the handle.

A primary use of the handle module is with a video blade shown in FIGS. 1 through 6. The blade in this instance comprises an elongate body extending between a coupling portion 68 and an opposing tip portion 70. A body is suitably shaped for insertion into the throat area or airway of a patient to provide access to the larynx area of the patient by extending through the pharynx region.

As in many conventional blade designs, the coupling portion 68 includes a body portion 72 arranged to be received between the two side plates of the coupling portion at the working end of the handle. A hook 74 formed on the body portion 72 is arranged to hook the blade onto the coupling pin of the handle. Spring pins 76 aligned along an axis parallel to the coupling pin but spaced therefrom are arranged for insertion into respective bores in the side plates in a coupled position to retain a mechanical connection between the blade and the handle. Depressing the spring pins 76 allows the hook to be unhooked from the coupling pin such that the blade is readily released from the handle and interchanged with a different blade having a body of different configuration but having a coupling portion of similar configuration for mating with the handle module.

The coupling portion of the blade also includes a positive contact 78, a negative contact 80 and a video output contact 82. The contacts of the coupling portion of the blade are arranged for alignment with respective contacts in the coupling portion at the working end of the handle module in a coupled position there-between. The contacts remain readily separable from one another for disengaging the contacts from one another automatically when the blade is mechanically released from the handle module.

In the illustrated embodiment, the body of the video blade includes a main portion 84 extending outward from the handle module so as to be inclined relative to the longitudinal axis of the handle. An outer tip portion extends outward from the main portion and curves back towards the handle such that the tip portion is inclined relative to the main portion 84.

A camera 86 is supported on the video blade in fixed relation therewith adjacent the tip portion such that the camera is readily separable from the handle module together with the separation of the video blade from the handle. Suitable conduits connect the camera 86 to the positive, negative and video output contacts of the coupling portion of the video blade for supplying electrical power to the camera and an integral LED light 88 of the camera and for relaying a video output signal generated by the camera back through the handle module to the monitor module.

Each set of negative, positive and video output contacts of the blade, handle and monitor modules are located within a respective insulated mating plate 90 such that the contacts are insulated from one another and remain inert when connected with other components of the kit which do not make use of the contacts. For example, conventional non-video enabled laryngoscope blades can be coupled to the handle module in which the conventional blade includes a similar hook 74 and spring pins 76 so as to be interchangeable with the video blade described above, but the contacts at the working end of the handle module remain disengaged from the conventional blade and remain insulated relative to one another so as to provide no function in this instance.

As described in FIGS. 7 and 8 however, in further embodiments, the handle may be provided with auxiliary conduits to supply a light signal to an auxiliary blade arranged for mechanical connection to the handle and which includes light conveying abilities but without the additional video function of a camera.

Turning now more particularly to the embodiment of FIG. 7, in this instance the handle includes an internal light source in the form of an LED which is connected to auxiliary electrical conduits 94 in the handle which communicate between the LED 92 and respective auxiliary contacts 96 at the output end of the handle as shown in broken line in FIG. 6. The auxiliary contacts 96 are arranged for alignment with respective auxiliary contacts of the monitor module in the coupled position there-between which are in turn coupled to the battery for supplying electrical power to the LED in the connected position. The LED in this instance directs light into an optical light guide 98 of the handle in the form of a fibre optic channel, a lens or other device for guiding light output from the LED to a suitable interface 100 in the base plate 26 of the coupling portion of the handle.

The auxiliary blade usable with the handle module in this instance and which is interchangeable with the video blade described above includes a fibre optic light guide extending along the body of the blade from the coupling portion to the tip portion. The inlet end of the light guide is arranged for alignment with the interface 100 in the base plate of the handle module in the coupled position to receive light from the interface and guide the light along the light guide to an outlet end for projecting the light from the tip of the blade.

Alternatively as shown in FIG. 8, the handle may be provided with a light conduit in the form of auxiliary electrical conduits 94 (shown in broken line in FIG. 6) connecting from the auxiliary contact at the output end to additional auxiliary contacts 104 at the working end so that the light signal communicated through the handle in this instance merely comprises electrical power supplied to an auxiliary blade interchangeable with the video blade noted above but which supports and LED thereon. The LED is fixed on the auxiliary blade for separation from the handle module together with the blade. Auxiliary contacts on the auxiliary blade align with the additional contacts 104 of the handle module in the coupled position between the blade and the handle module for supplying electrical power to the LED bulb which is located adjacent the tip portion to output light from the tip portion of the blade.

Turning now to FIGS. 9 through 12 there is illustrated a plurality of auxiliary blades and tools which are arranged to be interchangeably mounted on the working end of the handle module in place of the video blade or the alternative blades noted above. Whereas the blades in FIGS. 1-6 are Macintosh video blades which can be used as either a DL or a RIL, FIGS. 9-11 illustrate various possible RIL type video blades.

As shown in FIG. 9 an indirect video blade is provided with a coupling portion as described above and a main body portion 84 which is inclined relative to the longitudinal axis of the handle. The tip portion opposite the coupling portion locates the camera and the integral LED light source thereon to be oriented at an inclination to the main portion so as to be curved backward toward the handle.

In the embodiment of FIG. 10, in another indirect blade, the main portion of the blade extends substantially coaxially with the longitudinal axis of the handle with the tip portion again being inclined relative to the main portion and locating the camera and light thereon.

As shown in FIG. 11, a video blade is provided with a main portion inclined to the longitudinal axis of the handle and with a plurality of tube guides 108 at longitudinally spaced positions along the main portion and at the tip portion for supporting a tube alongside the blade.

As shown in FIG. 12, an auxiliary tool in the form of a stylet 110 is provided having a coupling portion 112 which is substantially identical to the body 72 of the coupling portion of the video blade described above so as to include a hook and spring pin for interchangeable connection with the handle module similarly to the blades noted above. An elongate probe 114 extends from the coupling portion 112 including a video conduit and a light conduit for operation of a camera and light at the free end or tip of the probe 114. The probe 114 is an elongate flexible member having a shape memory such that the probe is self supporting and is retained in any shape to which the probe is bent by the user.

Turning now to FIG. 13, there is illustrated a bronchoscope device 116 which is arranged for direct connection to the monitor module in place of the handle module. The device 116 thus includes a housing 118 having a coupling portion 120 at one end thereof which is suitably arranged for mating connection with the monitor module. The coupling portion 120 includes a positive contact, a negative contact and a video output contact for mating connection with the respective contacts of the monitor module in the same manner as the handle module. An elongate probe 122 extends from the housing 118 to support a camera and light at the free end thereof opposite the housing. The image generated by the camera is relayed back through the probe and appropriate conduits through the housing to relay a video signal through the video output contacts to the monitor module while electrical power is supplied to the camera and light through suitable electrical conduits. Suitable controls 124 are provided on the housing for steering the orientation of the probe 122 relative to the housing in a conventional manner found on prior bronchoscope devices. The housing and probe are also provided with appropriate suction and water supply controls 126 and the like which are also similar to conventional bronchoscope devices.

As described herein, the device that has been developed attempts to deal with some of the limitations of the current prior art devices. The device 10 is shown in the attached figures. The device is modular in design. There are three modules: the MONITOR MODULE, the HANDLE MODULE and the VIDEO MODULE. In its usual configuration the monitor module will be attached to the handle module which will be coupled to a standard direct laryngoscope blade, a Macintosh video blades or an indirect video blade. There are also peripherals available which will be attached directly to the video module, without the use of the handle module, this will be explained further below.

Monitor Module

The MONITOR MODULE consists of the video monitor and battery. This module is responsible for projecting the images of the glottis ultimately obtained from the video module. It is also the power supply for any of the devices peripherally attached to the monitor module directly or via the handle module. The monitor module's battery is rechargeable and the module should be attached to a dock or may be plugged in when not in use. This would allow the device to be recharged between uses. There will be two contact points outgoing from the monitor module. The first is the video contact point which ultimately transmits power to the CCD or CMOS camera and intrinsic light source at the patient interface. This happens either via the handle module or directly. The second contact point powers the DL light source and will be call the DL contact point. It powers the light source in a traditional, non-video blade via the handle module. This DL contact point is only used when the handle is used with standard non-video blades.

Ideally the monitor module should have the capability to be attached to an external monitor, have the ability to record images received in real time, auto-focusing and have adjustable brightness and contrast. The screen should also have an anti-glare coating/covering allowing for its use outside in the pre-hospital setting. The screen should also be articulated allowing for rotation about two axes allowing for adjustment to the users personal preference. The screen should also be visible from a wide variety of angles so that if the user needs to move his or her head relative to the screen's original positioning this would not sacrifice the view obtained on the monitor.

Handle Module

The handle module would come in three main configurations which could be purchased at the user's discretion. The first is a video-only handle module (video handle module). This handle module when attached to the monitor module would only have a video contact point and not have a second contact point. This type of handle could only be used with video blades and not with traditional non-video Macintosh or Miller type blades. The second type of handle module (video/fibre-optic handle module) would have two contact points, the video contact point and the DL contact point which would power an LED light at the distal end of the handle module. This type of handle module would allow this monitor/handle module configuration to work with both video blades and traditional non-video fibre-optic blades. These fibre-optic blades are currently the most commonly available blades in most hospitals. They utilize a light source at the handle which is transmitted via fiber-optics in the blade to the distal tip (hence the name). When the video/fiber-optic handle module is used with a non-video fiber-optic blade, the video contact point will not be in use while the LED light is in use. When the video/fiber-optic handle module is used with a video blade, the opposite is true. The third and final type of handle module is similar to the second type except that it would be for use with video blades and traditional non-video LED type blades (video/LED handle module). LED blades position the LED light at the end of the blade, vice the handle and the DL contact point at handle merely conducts power to the blade for the LED. The video/LED handle module will utilize the video contact point only when used with video blade and the DL contact point only when used with a LED type blade. As can be seen in FIG. 3, all handle module configurations utilize the universal attachment point currently used by all currently available DLs. This is what allows the handle module to work seamlessly with existing DL blades and video blades.

Video Module

In its preferred configuration the VIDEO MODULE would be a video blade, to be used with one of the three types of handle module described above. The video blade will not be specific to one of the handles above but rather will work with any of them. All blades will have a proximal attachment point where the video module interfaces with the handle module. This attachment point will be of the same configuration as the handle module which is of similar configuration to the universal laryngoscope blade attachment points found on existing non-video laryngoscopes. The video blade will have a distal tip which may be placed in the vallecula or posterior to the epiglottis depending on the blade design to allow a view of the glottis. Proximal to the distal tip of the video blade will be the camera and intrinsic light source. This will have an anti-fogging lens and will have a view of the distal tip and provide a wide view of the glottis and surrounding structures. Wires contained within the video blade will conduct power from the proximal end of the blade to the camera/light source and transmit the video image from the distal camera to the proximal video contact point.

The video blade size and shape will however be variable. The shape of the video blade would include standard Macintosh or Miller shaped video blades as depicted in FIGS. 1 through 5 which may be used in a direct or indirect manner. The video blade shape would also include video blades with more acute distal angulations which would be used in an indirect fashion with no direct capability. Blades may also have flanges which serve as tube guides if so desired by the end user. The size too would be variable for each specific shape. This would allow paediatric to adult sizing of blades, all of which could be used with the same monitor/handle module combination.

The video blade however is only one example of the possible video module configurations. Other possible video modules include a flexible video stylet as shown in FIG. 12. This video module could be attached to the handle module immediately following intubation where tube position is unclear. The gold standard for confirmation of tube placement in the trachea (and not the oesophagus) currently carbon dioxide detection in expiratory air. This is inaccurate in cardiac arrest patients where auscultation is generally used (with its own inherent flaws). In these cases a flexible video stylet attached directly on the handle module in standard fashion immediately following intubation could be used to confirm tube placement. This flexible video stylet would not be articulated and may or may not have channels for suction and irrigation available but would simply be placed through the ET tube in order to confirm visualization of the trachea and not the oesophagus. Currently the only similar option is a bronchoscope which is not available to most user and requires special training.

Another possible attachment would include an intubating video stylet. This would be attached onto the handle or directly to the monitor module. This attachment would be rigid but retain the ability to be shaped to a degree. The ET Tube would be placed over the intubating video stylet so that the distal tip of the stylet (inside of the ET tube) would be near the distal end of the ET Tube. A standard laryngoscope would be used to elevate the epiglottis and the tube would be introduced while using the video obtained on the monitor to guide the ET tube through the vocal cords.

Finally a bronchoscope video module attachment could easily be developed for use directly with the monitor module. The bronchoscope video module would have an articulated, illuminated distal tip, controlled via control knobs at the proximal end of the module. It would also have a variety of ports from the proximal to the distal end as with standard, currently available bronchoscopes, allowing users to do biopsies, suction, irrigation, etc. The user could utilize the monitor module for visualization of the working end of the device directly on the screen or output that image to a larger monitor as described above in the section on the monitor module.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A laryngoscopic device, the device comprising:
    a laryngoscope video blade comprising:
        an elongate body portion spanning between a coupling portion at a first end and a tip portion at an opposing second end so as to be arranged for insertion into an airway opening of a patient, the coupling portion including a positive contact, a negative contact, and a video output contact; and
        a camera supported on the body portion adjacent the tip portion so as to be arranged to generate a video signal, the camera being operatively connected to the positive contact, the negative contact, and the video output contact of the coupling portion of the laryngoscope video blade;
    an electrical power source including positive and negative terminals;
    a monitor module comprising a housing having a coupling portion and a video display monitor; and
    a handle module which is elongate between a working end and an opposing gripping end suited for gripping in a hand of a user;
    the working end of the handle module having a first coupling portion thereon in mating connection with the coupling portion of the laryngoscope video blade in a coupled position, the first coupling portion of the handle module and the coupling portion of the video blade being readily separable from one another from the coupled position so as to enable ready separation of the laryngoscope video blade from the handle module;
    the first coupling portion at the working end of the handle module including a positive contact, a negative contact and a video output contact supported thereon which are mated with respective ones of the positive contact, the negative contact and the video output contact of the laryngoscope video blade in the coupled position of the laryngoscope video blade with the handle module;
    the positive contact, the negative contact, and the video output contact of the working end of the handle module being separable from respective ones of the positive contact, the negative contact, and the video output contact of the laryngoscope video blade together with separation of the first coupling portion of the handle module from the coupling portion of the laryngoscope video blade; and
    the gripping end of the handle module having a second coupling portion thereon in mating connection with the coupling portion of the monitor module in a coupled position, the second coupling portion of the handle module and the coupling portion of the monitor module being readily separable from one another from the coupled position so as to enable ready separation of the monitor module from the handle module;
    the second coupling portion of the gripping end of the handle module including a video output which is adapted to communicate the video signal of the camera to the video display monitor in the coupled position so as to be arranged to display the video signal generated by the camera on the video display monitor;
    the video output of the handle module being separable from the video display monitor together with separation of the second coupling portion of the handle module from the coupling portion of the monitor module;
    the handle module further comprising a positive electrical conduit communicating between the positive contact of the working end of the handle module and the positive terminal of the power source, a negative electrical conduit communicating between the negative contact of the working end of the handle module and the negative terminal of the power source, and a video output conduit communicating between the video output contact at the working end of the handle and the video output at the gripping end of the handle module.

2. The laryngoscopic device according to claim 1 in combination with a laryngoscope auxiliary blade having an elongate body portion spanning between a coupling portion at a first end and a tip portion at an opposing second end and being shaped so as to be arranged for direct laryngoscopy, the coupling portion of the laryngoscope auxiliary blade being matingly connected to the first coupling portion of the handle module in a coupled position of the laryngoscope auxiliary blade, and the coupling portions being readily separable from one another from the coupled position such that the laryngoscope auxiliary blade is interchangeable with the laryngoscope video blade.

3. The laryngoscopic device according to claim 2 wherein the handle module includes a light source and the laryngoscope auxiliary blade includes an optical light guide in mating alignment with the light source of the handle module in the coupled position of the laryngoscope auxiliary blade on the handle module, the optical light guide being operable to convey light from the light source in the handle to the tip portion in the coupled position.

4. The laryngoscopic device according to claim 2 wherein the handle module includes auxiliary contacts at the working end and the auxiliary blade includes a light source at the tip portion which is connected to auxiliary contacts at the coupling portion of the auxiliary blade, the auxiliary contacts of the auxiliary blade and the auxiliary contacts of the working end of the handle module being arranged for mating alignment in the coupled position of the auxiliary blade on the handle module so as to be arranged to convey an electrical signal from the handle module to the light source of the auxiliary blade in the coupled position.

5. The laryngoscopic device according to claim 1 wherein the coupling portion at the working end of the handle module includes a coupling pin and a pair of sockets spaced from the coupling pin and wherein the coupling portion of the video blade includes a hook hooked onto the coupling pin in the coupled position and a pair of spring pins in releasable mating connection with the pair of sockets in the coupled position of the video blade on the handle module such that the video blade is interchangeable with a conventional laryngoscope blade having a hook and a pair of spring pins by releasing the spring pins.

6. The laryngoscopic device according to claim 1 wherein:
the monitor module supports the power source thereon and wherein the coupling portion of the monitor module and the second coupling portion at the gripping end of the handle module each comprise a positive contact, a negative contact, and a video output contact which are in mating connection with one another in the coupled position of the monitor module on the handle module;
the positive contact, the negative contact and the video output contact at the gripping end of the handle module are coupled to the positive electrical conduit, the negative electrical conduit and the video output conduit respectively; and
the positive contact, the negative contact and the video output contact of the monitor module being coupled to the positive terminal of the power source, the negative terminal of the power source and the video display monitor respectively.

7. The laryngoscopic device according to claim 6 in combination with a bronchoscope device comprising a coupling portion adapted to be coupled to the monitor module so as to be interchangeable with the handle module, the bronchoscope device including a camera arranged to generate a video signal, a video output contact connected to the camera which is arranged for mating connection with the video output contact of the monitor module in a coupled position of the monitor module on the bronchoscope device, and auxiliary electrical contacts arranged for mating connection with the positive and negative contacts of the monitor module so as to be arranged to supply electrical power to the camera of the bronchoscope device.

8. The laryngoscopic device according to claim 1 wherein the elongate body portion includes a main portion between the coupling portion and the tip portion which is inclined relative to a longitudinal axis of the handle module, the tip portion being inclined relative to the main portion.

9. The laryngoscopic device according to claim 1 wherein the elongate body portion includes a main portion between the coupling portion and the tip portion which is generally coaxial with a longitudinal axis of the handle module, the tip portion being inclined relative to the main portion.

10. The laryngoscopic device according to claim 1 wherein the elongate body portion includes a plurality of tube guides at spaced apart positions between the coupling portion and the tip portion so as to be arranged to support a tube member alongside the body portion.

11. The laryngoscopic device according to claim 1 in combination with a stylet device comprising a coupling portion configured similarly to the coupling portion of the video blade such that the video blade and the stylet device are arranged to be interchangeably mounted on the handle module, the stylet device further comprising a probe member supporting a camera at a tip portion thereof opposite the coupling portion, the camera being connected to a video output contact at the coupling portion of the stylet device which is arranged for mating alignment with a video output contact on the working end of the handle module in a coupled position of the stylet on the handle module so as to be arranged for communicating a video signal generated by the camera of the stylet to the video output conduit of the handle module.

12. A laryngoscopic device for use with a video display monitor, the device comprising:
a first laryngoscope blade in the form of a laryngoscope video blade comprising:
an elongate body portion spanning between a coupling portion at a first end and a tip portion at an opposing second end so as to be arranged for insertion into an airway opening of a patient, the coupling portion including a positive contact, a negative contact, and a video output contact; and
a camera supported on the body portion adjacent the tip portion so as to be arranged to generate a video signal, the camera being operatively connected to the positive contact, the negative contact, and the video output contact of the coupling portion of the laryngoscope video blade;
an electrical power source including positive and negative terminals;
a handle module which is elongate between a working end and an opposing gripping end suited for gripping in a hand of a user;
the working end of the handle module having a coupling portion thereon in mating connection with the coupling portion of the laryngoscope video blade in a coupled position, the coupling portion of the handle module and the coupling portion of the video blade being readily separable from one another from the coupled position so as to enable ready separation of the laryngoscope video blade from the handle module;
the coupling portion at the working end of the handle module including a positive contact, a negative contact and a video output contact supported thereon which are mated with respective ones of the positive contact, the negative contact and the video output contact of the laryngoscope video blade in the coupled position of the laryngoscope video blade with the handle module;
the positive contact, the negative contact, and the video output contact of the handle module being separable from respective ones of the positive contact, the negative contact, and the video output contact of the laryngoscope video blade together with separation of the coupling portion of the handle module from the coupling portion of the laryngoscope video blade; and
the handle module further comprising a positive electrical conduit communicating between the positive contact of the working end of the handle module and the positive terminal of the power source, a negative electrical conduit communicating between the negative contact of the working end of the handle module and the negative terminal of the power source, and a video output conduit communicating between the video output contact at the working end of the handle and a video output of the handle module which is adapted to communicate the video signal of the camera to the video display monitor; and
a second laryngoscope blade in the form of a direct laryngoscope blade, different in configuration than the first laryngoscope blade, having an elongate body portion spanning between a coupling portion at a first end and a tip portion at an opposing second end and being shaped so as to be adapted to perform direct laryngoscopy, the coupling portion of the direct laryngoscope blade being adapted to be matingly connected to the coupling portion of the handle module in a coupled position of the second laryngoscope blade such that the coupling portions remain readily separable from one another from the coupled position;

whereby the video laryngoscope blade and the direct laryngoscope blade are interchangeable with one another on the coupling portion of the handle module.

13. The laryngoscopic device according to claim 12 wherein the laryngoscope video blade is a direct video laryngoscope blade adapted to perform direct laryngoscopy.

14. The laryngoscopic device according to claim 12 wherein the laryngoscope video blade is a indirect video laryngoscope blade.

15. The laryngoscopic device according to claim 12 further comprising a third laryngoscope blade, different in configuration than the first laryngoscope blade and the second laryngoscope blade, having an elongate body portion spanning between a coupling portion at a first end and a tip portion at an opposing second end and a plurality of tube guides on the elongate body portion at spaced apart positions between the coupling portion and the tip portion so as to be arranged to support a tube member alongside the body portion, the coupling portion of the third laryngoscope blade being adapted to be matingly connected to the coupling portion of the handle module in a coupled position of the second laryngoscope blade such that the coupling portions remain readily separable from one another from the coupled position whereby the first laryngoscope blade, the second laryngoscope blade, and the third laryngoscope blade are interchangeable with one another on the coupling portion of the handle module.

* * * * *